US008378312B1

(12) United States Patent
Gordon et al.

(10) Patent No.: US 8,378,312 B1
(45) Date of Patent: Feb. 19, 2013

(54) SYSTEM, APPARATUS AND METHOD FOR DEFLECTING A PARTICLE BEAM

(75) Inventors: John Gordon, Henfield (GB); Raymond Paul Boisseau, Waltham, MA (US); Andrew Dart, Swampscott, MA (US)

(73) Assignee: Pyramid Technical Consultants, Inc., Lexington, MA (US)

(*) Notice: Subject to any disclaimer, the term of this patent is extended or adjusted under 35 U.S.C. 154(b) by 0 days.

(21) Appl. No.: 13/214,118

(22) Filed: Aug. 19, 2011

(51) Int. Cl.
*H01J 29/70* (2006.01)
*H01J 29/51* (2006.01)
*H01F 7/18* (2006.01)

(52) U.S. Cl. ............. 250/396 R; 250/298; 250/396 ML; 313/413; 313/421; 313/431; 313/440; 315/5.35; 315/268.28; 335/209; 335/210; 335/268

(58) Field of Classification Search .................. 250/298, 250/306, 307, 309–311, 396 ML, 396 R, 250/492.1, 492.2, 492.21, 492.22, 492.23, 250/492.3; 313/409, 413, 414, 416, 419, 313/421, 425, 427, 431, 435, 440, 44; 335/209, 335/210, 212, 213, 214, 230, 243, 246, 268, 335/289, 306; 315/5, 24, 5.26, 5.29, 5.35, 315/364, 368.25–368.28, 397, 399, 403, 315/5.24, 403.4
See application file for complete search history.

(56) References Cited

U.S. PATENT DOCUMENTS

| | | | | | |
|---|---|---|---|---|---|
| 3,886,398 | A | * | 5/1975 | Feinstein | 315/5 |
| 4,162,403 | A | * | 7/1979 | Baumgarten | 250/396 ML |
| 4,396,897 | A | * | 8/1983 | Sluijterman et al. | 335/212 |
| 4,902,994 | A | * | 2/1990 | Kawamura | 335/210 |
| 5,350,926 | A | * | 9/1994 | White et al. | 250/492.21 |
| 5,834,786 | A | * | 11/1998 | White et al. | 250/492.21 |
| 6,097,163 | A | * | 8/2000 | Chauvin et al. | 315/368.26 |
| 7,078,713 | B2 | * | 7/2006 | White | 250/492.21 |
| 8,035,087 | B2 | * | 10/2011 | White | 250/396 ML |
| 2005/0017202 | A1 | * | 1/2005 | White | 250/492.21 |
| 2005/0109879 | A1 | * | 5/2005 | Patterson | 244/172 |
| 2008/0067397 | A1 | * | 3/2008 | Tsukihara et al. | 250/396 ML |
| 2009/0218506 | A1 | * | 9/2009 | Nakasuji et al. | 250/396 ML |
| 2010/0001204 | A1 | * | 1/2010 | White | 250/398 |
| 2010/0213384 | A1 | * | 8/2010 | Furukawa et al. | 250/396 ML |
| 2011/0101236 | A1 | * | 5/2011 | Cameron et al. | 250/396 ML |

* cited by examiner

*Primary Examiner* — Bernard E Souw

(57) ABSTRACT

A variety of systems, apparatus and methods for deflecting a particle beam are described. An apparatus comprises at least six electromagnetic portions disposed on a plane. Each of the at least six electromagnetic portions is aligned with a radius emanating from an axis normal to the plane and is distanced from the axis to form a volume about the axis. At least six coils are configured for affecting a dipole magnetic field in the volume in response to electrical currents applied to physically opposing coils where a particle beam entering the volume is deflected. Each of the at least six coils is disposed about a one of the at least six electromagnetic portions. A yoke structure is configured for returning a generated magnetic flux.

20 Claims, 12 Drawing Sheets

SYSTEM, APPARATUS AND METHOD FOR DEFLECTING A PARTICLE BEAM

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to implementations of electromagnetic apparatus. More particularly, the invention relates to delivering a charged particle beam to arbitrary points in a region, such as for particle therapy in medical applications.

BACKGROUND OF THE INVENTION

Many applications, including medical therapy and diagnostics, semiconductor processing and industrial radiography require beams of particles to be directed to particular positions with good accuracy, and with repeatable and timely control. A particular application where accurate scanning and positioning of high energy particle beams may be required is particle therapy. For particle therapy, beams of high energy charged particles, most often protons, but also heavier ions such as ionized carbon, oxygen and argon, may be used to deliver a therapeutic dose. Particle therapy may offers improvements over more conventional X-ray therapy by being able to deliver a dose much more precisely to a region within the body and with reduced unwanted damage to healthy tissues surrounding the region.

A method of particle beam therapy providing precise control and the ability to deliver a dose to the most complex volumetric shapes is pencil beam scanning. For pencil beam scanning, a narrow beam of mono-energetic particles may be deflected by controlled amounts so as to describe a pattern in space. For pencil beam scanning, angular deflection is typically less than ten degrees. In combination with modulation of the beam intensity and sequential delivery of patterns at different beam energies, a desired dose distribution may be achieved. Several such exposures may be performed over a period of days or weeks in order to complete a treatment plan.

A component of a pencil beam scanning system is the electromagnets that deflect the beam to the desired trajectory. These electromagnets may require timely magnetic field changes in order to develop a desired pattern without experiencing undue periods of time for the magnetic field to settle. These electromagnets may be required to deliver good ion optical qualities over the scanned portions in order to avoid disruption of the beam shape. These electromagnets should not occupy excessive space in the trajectory of the beam, as this may translate into a larger system, potentially higher costs, and may preclude the installation of systems in some locations. In order to support a broad array of treatments, the electromagnets should not impose arbitrary constraints for how the beam trajectory may be manipulated.

FIG. 1 presents an example illustration of a conventional electromagnetic apparatus for deflecting a charged particle beam.

A deflecting mechanism 100 includes a horizontal electromagnetic portion 102 and a vertical electromagnetic portion 104. The terms horizontal and vertical are used for convenience only and do not represent actual positions.

Deflecting mechanism 100 may operate to deflect the trajectory of a charged particle 106 in the horizontal direction via horizontal electromagnetic portion 102 and in the vertical direction via vertical electromagnetic portion 104. Not shown is a typical yoke for returning magnetic flux from portions 102 and 104.

Horizontal electromagnetic portion 102 may operate to generate a magnetic field in the vertical direction and vertical electromagnetic portion 104 may operate to generate a magnetic field in the horizontal direction.

Charged particle 106 may initially be moving in the direction of an axis 108. After transitioning through horizontal electromagnetic portion 102 and vertical electromagnetic portion 104, charged particle 106 may be moving in a different trajectory as denoted by a trajectory 110.

High quality dipole fields, with minimal higher order components, may be established via simple designs as illustrated in FIG. 1. Furthermore, beam aberrations introduced by the electromagnetic portions may be considered small. The operation of the two electromagnetic portions may be distinct. For example, horizontal electromagnetic portion 102 may have an air gap 112 where the magnetic field generated may be slightly greater than the dimension of the received beam of particles. In contrast, vertical electromagnetic portion 104 may have an air gap 114 which has a larger separation distance than exhibited by air gap 112 in order to accommodate the range of deflections generated by horizontal electromagnetic portion 102. Furthermore, the increased separation distance require for air gap 114 may require additional amp-turns for an energizing circuit 116 and may translate into a slower beam movement in the vertical direction generated via vertical electromagnetic portion 104. The increased air gap and increased amp-turns may result in more complexity for planning the map of potential beam positions due to differing speed of response of the in the horizontal and vertical axes. Furthermore, the conventional deflection apparatus, as illustrated in FIG. 1, may require an apparatus occupying increased space, which may be considered a premium for many systems.

FIG. 2 presents an example illustration of a conventional method and means for deflecting a charged particle using an electromagnetic apparatus.

A deflecting mechanism 200 includes a horizontal electromagnetic portion 202 and a vertical electromagnetic portion 204.

Deflecting mechanism 200 may operate to deflect the trajectory of a charged particle 206 in the horizontal direction via horizontal electromagnetic portion 202 and in the vertical direction via vertical electromagnetic portion 204. Horizontal electromagnetic portion 202 and vertical electromagnetic portion 204 may be configured as a quadrupole structure.

Horizontal electromagnetic portion 202 may operate to generate a magnetic field in the vertical direction and vertical electromagnetic portion 204 may operate to generate a magnetic field in the horizontal direction.

Charged particle 206 may initially be moving in the direction of an axis 208. After transitioning through horizontal electromagnetic portion 202 and vertical electromagnetic portion 204, charged particle 206 may be moving in a different trajectory as denoted by a trajectory 210.

The physical size for a two dipole design as illustrated in FIG. 1 may be reduced by superimposing the vertical and horizontal electromagnetic portions to create a quadrupole structure as illustrated in FIG. 2. The excitation of the electromagnetic portions for the quadrupole as illustrated in FIG. 2 may be dissimilar from that of a conventional beam focusing quadrupole. A conventional beam focusing quadrupole may be configured with four coils and a single power supply, with the direction of the current flow through the coils arranged to generate a zero magnetic field on the central axis of the magnetic air gap and a linearly increasing magnetic field with increased displacement from the central axis to shape the beam cross-section.

The superimposed dipole as illustrated with reference to FIG. 2 may be configured with two independent power supplies with one power supply associated with an opposed electromagnetic portion. The resultant magnetic field for the superimposed dipole may be considered as a vector sum of the fields of the two individual dipoles associated with the composite structure. The superimposed deflection apparatus may be controlled similar to two independent dipoles with one deflecting in the horizontal direction and one deflecting in the vertical direction. A square configuration for the electromagnetic portions is common, as other structures and configurations may result in a poor quality dipole magnetic field associated with the central axis and may also result in large pole spacing. However, even a square configuration for the superimposed dipole may result in a magnetic field which may be of considerably less quality than realized with equivalent separate dipoles as illustrated with reference to FIG. 1. Furthermore, as a result of the less quality magnetic field generated by the superimposed dipole, beam aberrations may be experienced.

In view of the foregoing, there is a need for improved techniques for electromagnets associated with deflecting charged particle beams.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
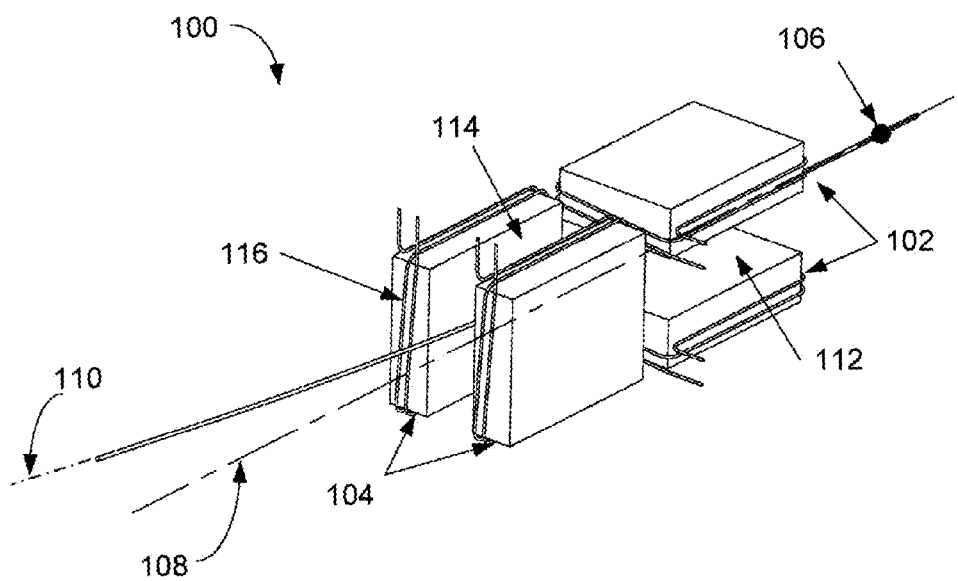
FIG. 1 presents an example illustration of a conventional electromagnetic apparatus for deflecting a charged particle beam.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Embodiments of the present invention will be described which provide means and methods for delivering a charged particle beam to arbitrary points in a region controlled by small angle deflection of the charged particle beam. A non-limiting example of an application for deflection and delivery of a charged particle beam includes particle therapy associated with the practice of medicine. A multi-pole electromagnet when disposed with an appropriate excitation may operate to steer a charged particle beam with energy in a typical range of 60 MeV to 6 GeV, via a sequence of trajectories in order to deliver an ion beam to desired positions located in a transverse surface located at a distance from the electromagnet. The multi-pole electromagnet may be connected to a multiplicity of power amplifiers. The power amplifiers may be connected to opposing coils associated with the multi-pole electromagnet. Furthermore, the multiplicity of power amplifiers may be connected to a power supply. As an example associated with particle beam therapy, the control of particle beam position combined with kinetic energy adjustment may operate to control the lateral distribution and range of particles projected into a body. Furthermore, modulation of the particle beam intensity may allow a desired volumetric dose distribution to be delivered. The multi-pole electromagnet, via appropriate currents applied to the coils of the electromagnet, may operate to position a charged particle beam at a location associated with a traverse plane defined in polar coordinates as R and θ. For sinusoidal currents applied to six or more coils as a function of the pole angles, the resulting magnetic field created between the coils may provide a good quality dipole magnetic field which can be rotated to any arbitrary angle. Furthermore, the size of associated electromagnets may be reduced, and higher quality beams may be produced as compared to conventional means and methods.

In other embodiments of the present invention, methods and means will be described for providing a multi-pole electromagnet with modified tips for improving the quality of the generated magnetic field. The modified tips may be configured with various geometric shapes. Non-limiting examples of geometric shapes include circular and elliptical.

In other embodiments of the present invention, methods and means will be described for providing a multi-pole electromagnet with modified air gaps for providing greater clearance for a charged particle beam, resulting in less likelihood of sustaining particle beam losses.

In other embodiments of the present invention, methods and means will be described for providing magnetic field probes for providing feedback in order to support systems operating with non-linear configurations.

Figure 3:
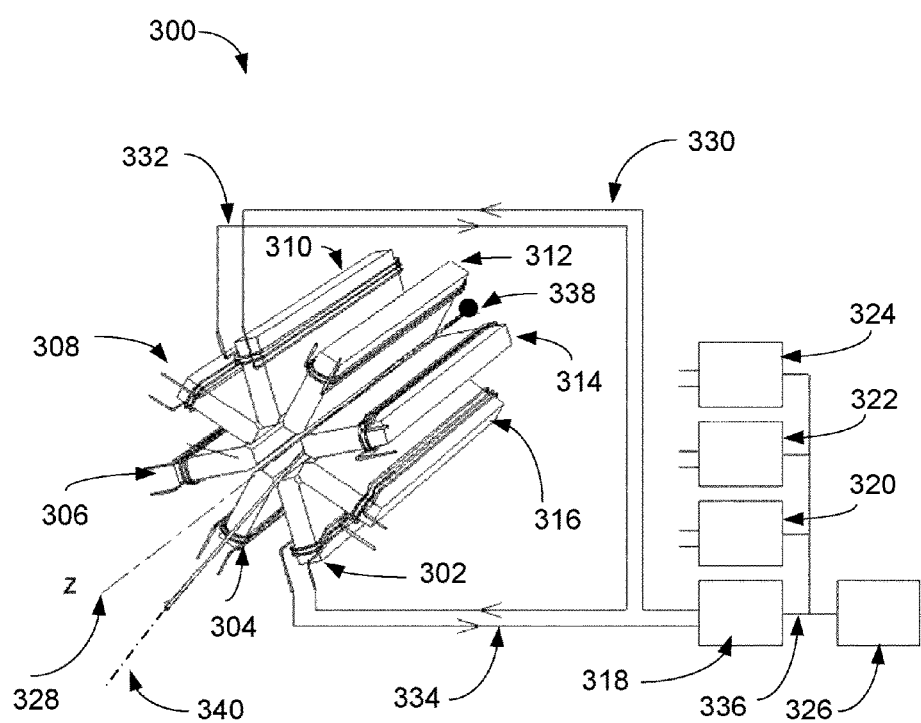
FIG. 3 presents an illustration of an example multi-pole deflection apparatus for deflecting a charged particle, in accordance with an embodiment of the present invention.

FIG. 3 presents an illustration of an example multi-pole deflection apparatus for deflecting a charged particle, in accordance with an embodiment of the present invention.

A multi-pole deflection apparatus 300 may operate to deflect a received charged particle via a generated magnetic field. For simplicity, a yoke for magnetic flux return is not shown.

Multi-pole deflection apparatus 300 includes an electromagnetic portion 302, an electromagnetic portion 304, an electromagnetic portion 306, an electromagnetic portion 308, an electromagnetic portion 310, an electromagnetic portion 312, an electromagnetic portion 314, an electromagnetic portion 316, an amplifier 318, an amplifier 320, an amplifier 322, an amplifier 324 and a power supply 326. As a non-limiting example, power supply 326 may be configured as Direct Current (DC).

Electromagnetic portions 302, 304, 306, 308, 310, 312, 314 and 316 may operate to generate an associated magnetic field. Amplifier 318, 320, 322, 324 may operate to provide amplified power. Power supply 326 may operate to provide electrical power.

The electromagnetic portions may be configured in a circular fashion about a z-axis 328.

A first node of electromagnetic portion 310 may be connected to a first node of amplifier 318 via a conductor 330. A second node of electromagnetic portion 310 may be connected to a first node of electromagnetic portion 302 via a conductor 332. A second node of electromagnetic portion 302 may be connected to a second node of amplifier 318 via a conductor 334. Electromagnetic portion 302 and electromagnetic portion 310 may be configured as physically opposing.

Electromagnetic portions 302, 304, 306, 308, 310, 312, 314 and 316 may be configured and connected (not shown) to amplifiers 320, 322 and 324 in a similar fashion as described previously with reference to electromagnetic portion 302, 310, amplifier 318 and conductors 330, 332 and 334.

Amplifiers 318, 320, 322 and 324 may be connected to power supply 326 via a power conduit 336.

A charged particle 338 may initially be moving in the direction of z-axis 328. After transitioning through electromagnetic portions 302, 304, 306, 308, 310, 312, 314 and 316 and subjected to a dipole magnetic field located in the central channel of multi-pole deflection apparatus 300, charged particle 338 may be moving in a different trajectory as denoted by a trajectory 340.

The operation of multi-pole deflection apparatus 300 with appropriated electrical currents traversing the coils of electromagnetic portions 302, 304, 306, 308, 310, 312, 314 and 316 may provide a high quality dipole magnetic field.

For the number of electromagnetic portions six or greater and a pattern of currents with an associated sinusoidal function of the pole angles, a high quality dipole magnetic field may be created which can be rotated to any angle.

Figure 2:
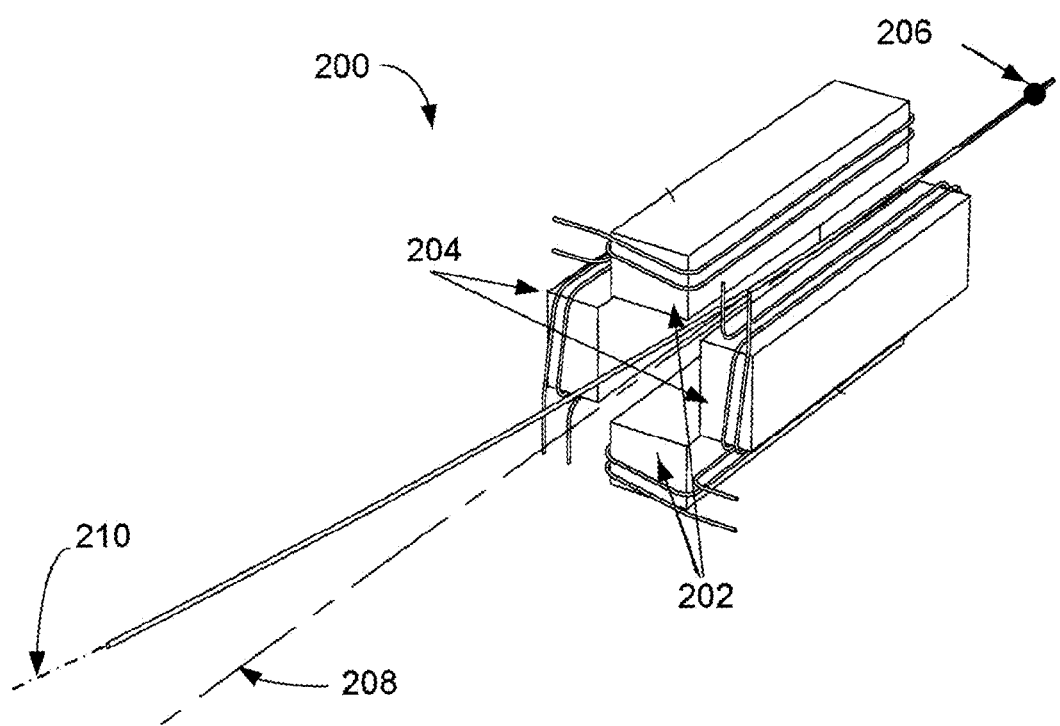
FIG. 2 presents an example illustration of a conventional method and means for deflecting a charged particle using an electromagnetic apparatus.

The present invention combines the small physical size of the quadrupole structure as illustrated with reference to FIG. 2 and the high quality magnetic field of the dipole pair as illustrated with reference to FIG. 1.

Figure 4:
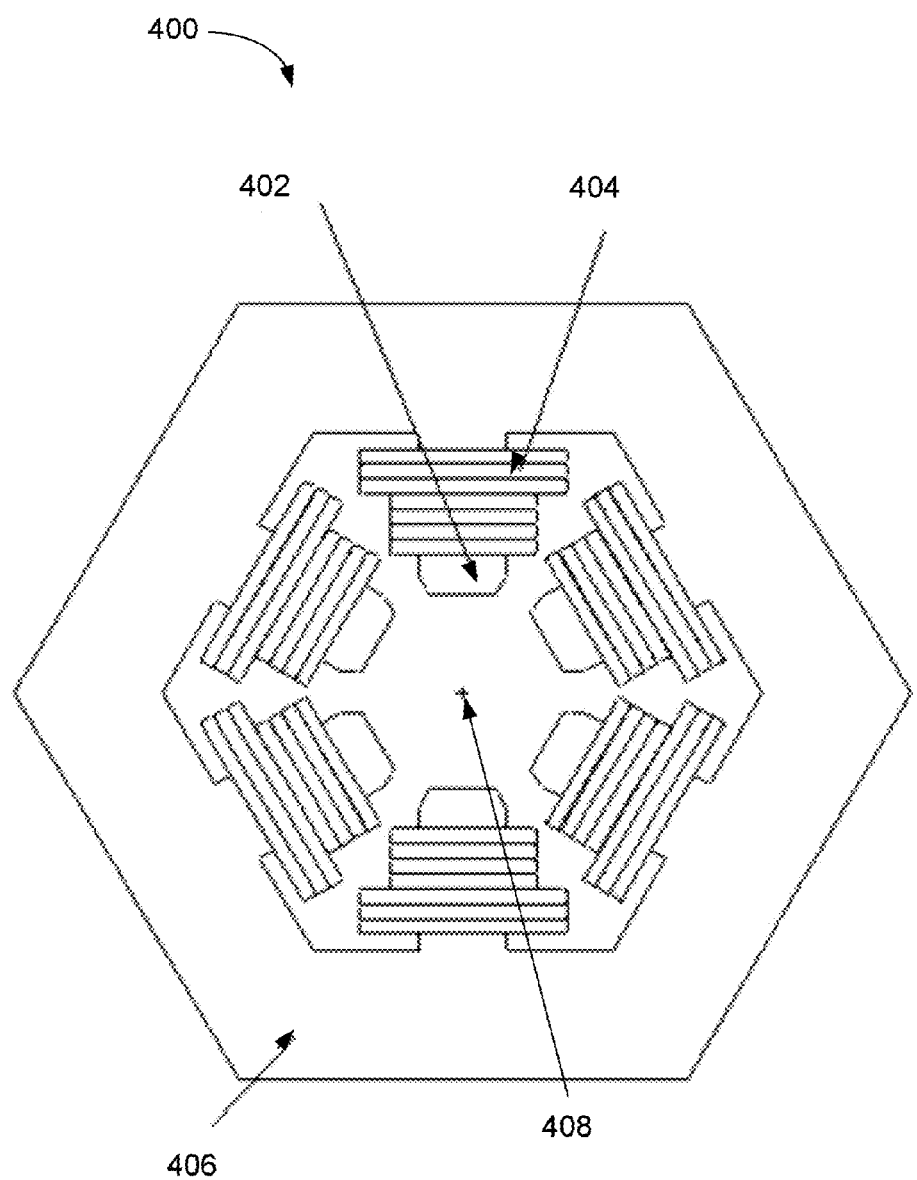
FIG. 4 presents a cross-section illustration of an example sextupole deflection apparatus for deflecting a charged particle, in accordance with an embodiment of the present invention.

FIG. 4 presents a cross-section illustration of an example sextupole deflection apparatus for deflecting a charged particle, in accordance with an embodiment of the present invention.

A sextupole deflection apparatus 400 includes six electromagnetic portions with a sampling denoted as an electromagnetic portion 402, six coils with a sampling denoted as a coil 404 and a yoke structure 406. Non-limiting examples of materials for constructing yoke structure 406 include iron and steel.

The six electromagnetic portions may be arranged in a circle about a central axis 408. Magnetization may be produced by applying electrical currents to electrical coils for opposing electromagnetic portions using three independent power amplifiers (connections between coils and amplifiers not shown). A desired dipole magnetic field may be created in the region enclosed by the electromagnetic portions. The created magnetic flux may be returned via yoke structure 406.

Figure 5:
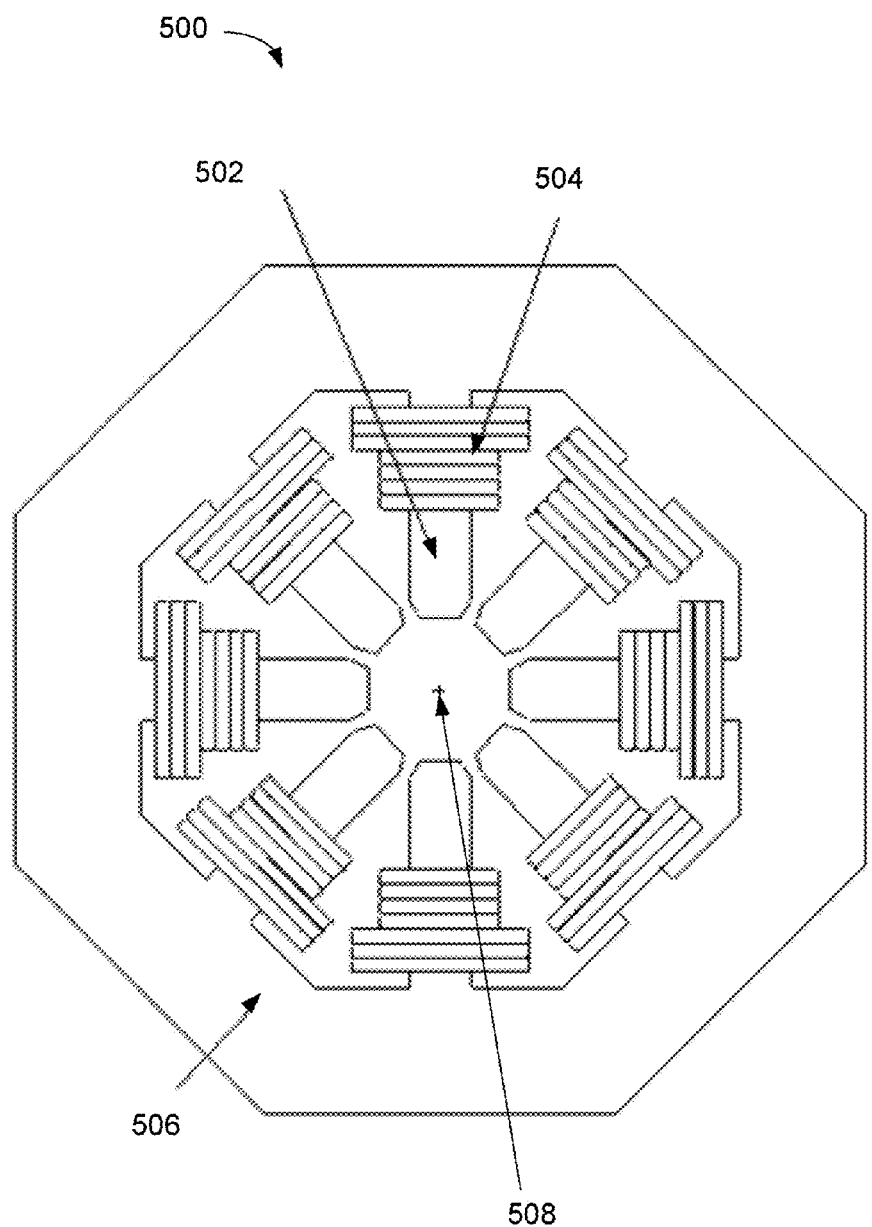
FIG. 5 presents a cross-section illustration of an example octupole deflection apparatus for deflecting a charged particle, in accordance with an embodiment of the present invention.

FIG. 5 presents a cross-section illustration of an example octupole] deflection apparatus for deflecting a charged particle, in accordance with an embodiment of the present invention.

An octupole deflection apparatus 500 includes eight electromagnetic portions with a sampling denoted as an electromagnetic portion 502, eight coils with a sampling denoted as a coil 504 and a yoke structure 506. Non-limiting examples of materials for constructing yoke structure 506 include iron and steel.

The eight electromagnetic portions may be arranged in a circle about a central axis 508. Magnetization may be produced by applying electrical currents to electrical coils for opposing electromagnetic portions using four independent power amplifiers (connections between coils and amplifiers not shown). A desired dipole magnetic field may be created in the region enclosed by the electromagnetic portions. The created magnetic flux may be returned via yoke structure 506.

The dipole magnetic quality increases with the number of electromagnetic portions, but so does the complexity of the apparatus (e.g. number of power amplifiers required—one for every opposing electromagnetic portion). Common applications for the present invention may be configured with six or eight electromagnetic portions.

Figure 6:
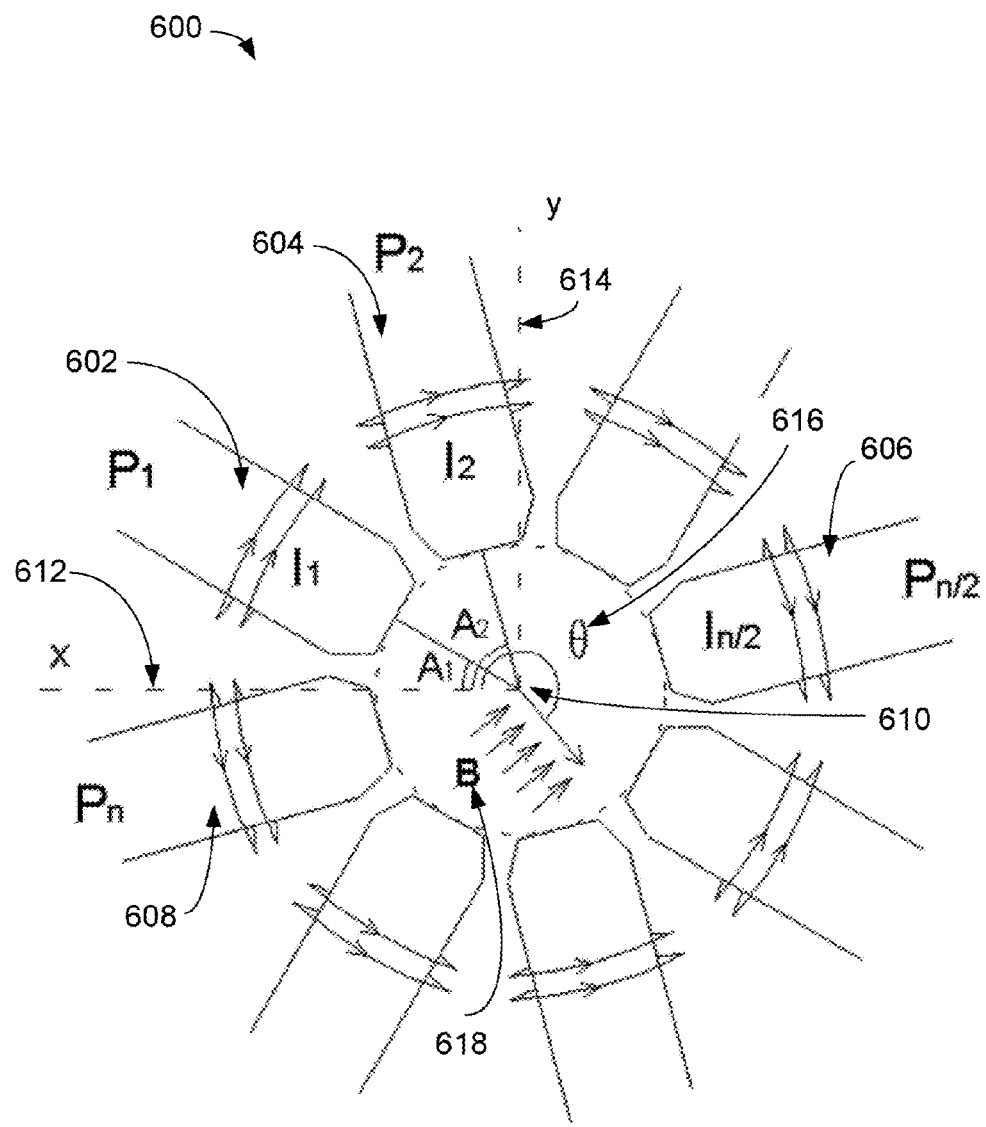
FIG. 6 presents a geometrical illustration for calculating coil currents for an example n-pole deflection apparatus for deflecting a charged particle, in accordance with an embodiment of the present invention.

FIG. 6 presents a geometrical illustration for calculating coil currents for an example n-pole deflection apparatus for deflecting a charged particle, in accordance with an embodiment of the present invention.

A deflection apparatus 600 includes n electromagnetic portions with a sampling denoted as an electromagnetic portion 602, an electromagnetic portion 604, an electromagnetic portion 606 and an electromagnetic portion 608.

The excitation pattern for the associated coils of the electromagnetic portions for deflection apparatus 600 for steering a charged particle via a high quality dipole field may be explained with reference to FIG. 6.

The electromagnetic portions may be configured in a circle about a z-axis 610 with z-axis 610 projected into the page. Furthermore, electromagnetic portions may be configured with respect to an x-axis 612 directed to the left with respect to the page and a y-axis 614 directed vertically upwards with respect to the page.

A charged particle (not shown) may enter deflection apparatus 600 parallel and in close proximity to z-axis 610. Magnetic poles, denoted as $P_k$, k=1 to n, associated with n magnetic portions may be arranged in a circular array at angles, denoted as $A_k$, with respect to x-axis 612. A positive charged particle deflection angle, denoted as an angle 616, resulting from a uniform dipole field 618 may be generated by coil currents denoted as $I_k$, k=1 to n/2.

The zero degrees direction of particle deflection may be taken to be along x-axis 612. Angle 616 may be considered as the direction of deflection relative to zero degrees with respect to x-axis 612. A deflection for a positive ion with a value of 0 degrees for angle 616 may be associated with magnetic field vectors for uniform dipole field 618 rotated from the arbitrary angle illustrated so that they are pointing from the top of the page to the bottom of the page and positioned in the plane of the page. Furthermore, the n magnetic poles $P_k$, k=1 to n, may be arranged in a circular array with an even value for n. Furthermore, the first n/2 magnetic pole tips may be centered at angles $A_k$, k=1 to n/2, with an increasing positive angle denoted in the clockwise direction. Furthermore, corresponding opposing magnetic portions may be positioned at $A_k+180$ degrees. Furthermore, every opposing pole pair may be powered by a single power amplifier whereby coils may be connected in series such that the same electrical current may traverse the coil pairs. Furthermore, the operation may be considered similar as in the case of a conventional magnetic dipole deflection apparatus. For purposes of explanation and as a non-limiting example, the magnetic poles and coils may be identical and arranged at regular angles starting from zero degrees, however, any known configuration may be considered.

A regular distribution of magnetic poles about z-axis 610 may operate to generate a high quality magnetic field. To generate a particular dipole magnetic field for deflecting a charged particle zero degrees for angle 616, the exciting currents $I_k$, k=1 to n/2 may be represented by Equation (1) as shown below:

$$I_k = I_p * \sin(-A_k) \quad (1)$$

For Equation (1), $I_p$ may represent a particular electrical current determining an amount of deflection to be applied in the direction associated with the magnetic pole. A positive value for the electrical current for $I_p$ may be associated with a clockwise flow of electrical current when viewing a magnetic portion from z-axis 610. A negative value for $I_p$ may be associated with a counter-clockwise flow of electrical current when viewing a magnetic portion from z-axis 610. Furthermore, a coil for a pole may be considered as similar and connected in series with a coil 180 degrees opposed, in a fashion similar to a conventional dipole magnet. In order to rotate the dipole magnetic field direction for producing a deflection in another direction θ, the excitation for $I_k$, k=1 to n/2 may be represented as Equation (2) as shown below:

$$I_k = I_p * \sin(\theta - A_k) \quad (2)$$

The variable θ may be associated with any known value. Furthermore, the rotation of the magnetic field may be associated with any direction and as a result, the deflection direction may also be associated with any direction. Furthermore, the magnitude of the dipole magnetic field may remain constant, independent of θ.

Figure 7:
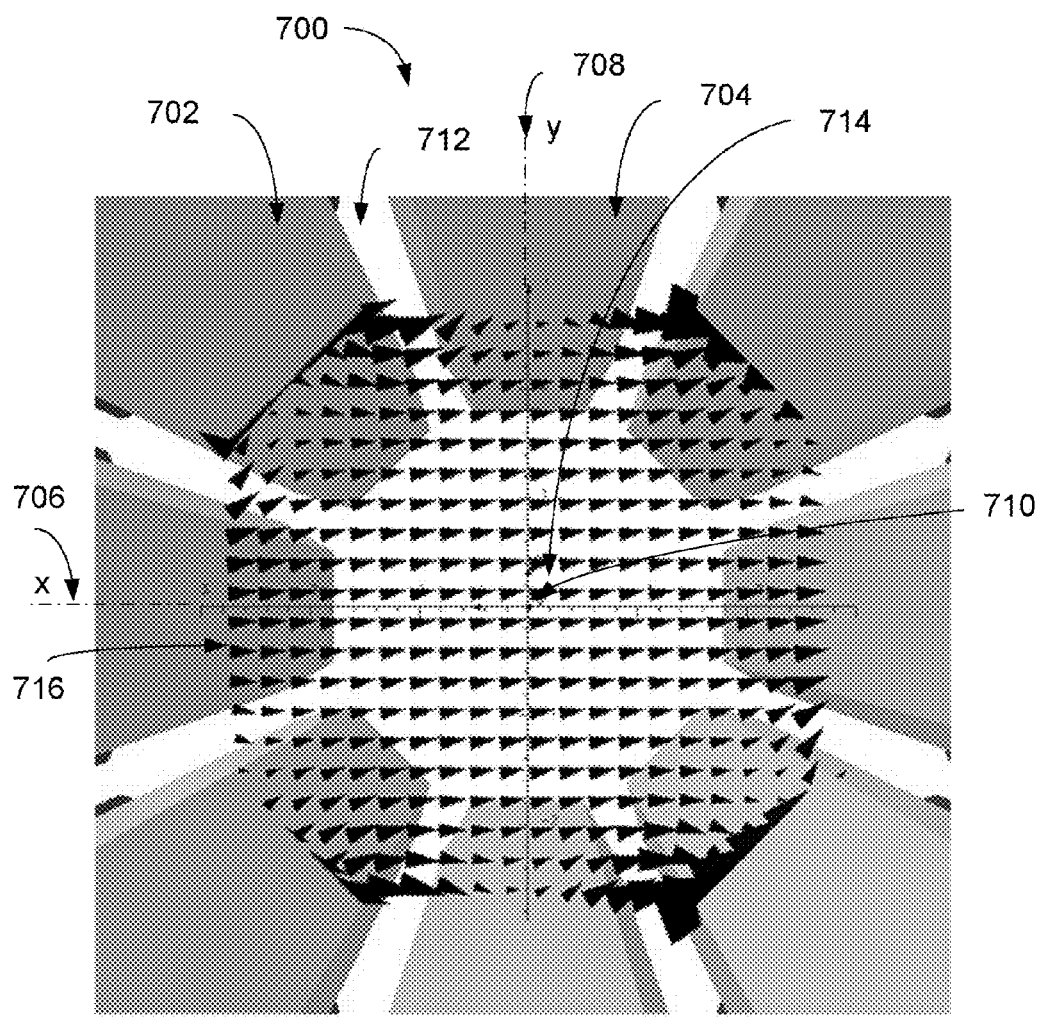
FIG. 7 presents an example illustration of traverse plane magnetic field vectors associated with the bore of a multi-pole electromagnetic apparatus, in accordance with an embodiment of the present invention.

FIG. 7 presents an example illustration of traverse plane magnetic field vectors associated with the bore of a multi-pole electromagnetic apparatus, in accordance with an embodiment of the present invention.

A multi-pole electromagnetic apparatus 700 includes a multiplicity of electromagnetic tip portion with a sampling denoted as an electromagnetic tip portion 702 and an electromagnetic tip portion 704.

Multi-pole electromagnetic apparatus 700 may be oriented with respect to an x-axis 706, a y-axis 708 with a z-axis 710 projected into the page.

The electromagnetic tip portions may be separated by a multiplicity of gaps with a sampling denoted as a gap 712. For example, gap 712 may be located between electromagnetic tip portion 702 and electromagnetic tip portion 704. Furthermore, the electromagnetic tip portions may be located such as to surround a bore area 714.

A magnetic field may be created by multi-pole electromagnetic apparatus 700 with the resultant magnetic field illustrated by a multiplicity of magnetic field vectors with a sampling denoted as a field vector 716. Magnetic field vectors presented as black arrow heads may be oriented at a traverse plane with respect to multi-pole electromagnetic apparatus 700. The equal magnitude and direction orientation for the magnetic field vectors illustrates the quality of the dipole magnetic field. For example, the more diversity observed for the magnetic field vectors with respect to magnitude and direction orientation, the less the quality of magnetic field generated. For this example, the calculation for coil current pattern produced a deflection angle of 260 degrees, which illustrates that there may be no constraint that the field direction is aligned with the angular arrangement of the electromagnetic tip portions.

The illustration presented by FIG. 7 provides a visual indication of the dipole magnetic field quality for a magnetic field rotated to an arbitrary angle. The associated magnetic field quality may be confirmed quantitatively by evaluating Legendre polynomial coefficients for the region where charged particles may travel and by measuring the aberrations introduced into a known beam transverse profile resulting from the beam traversing through multi-pole electromagnetic apparatus 700.

Figure 8:
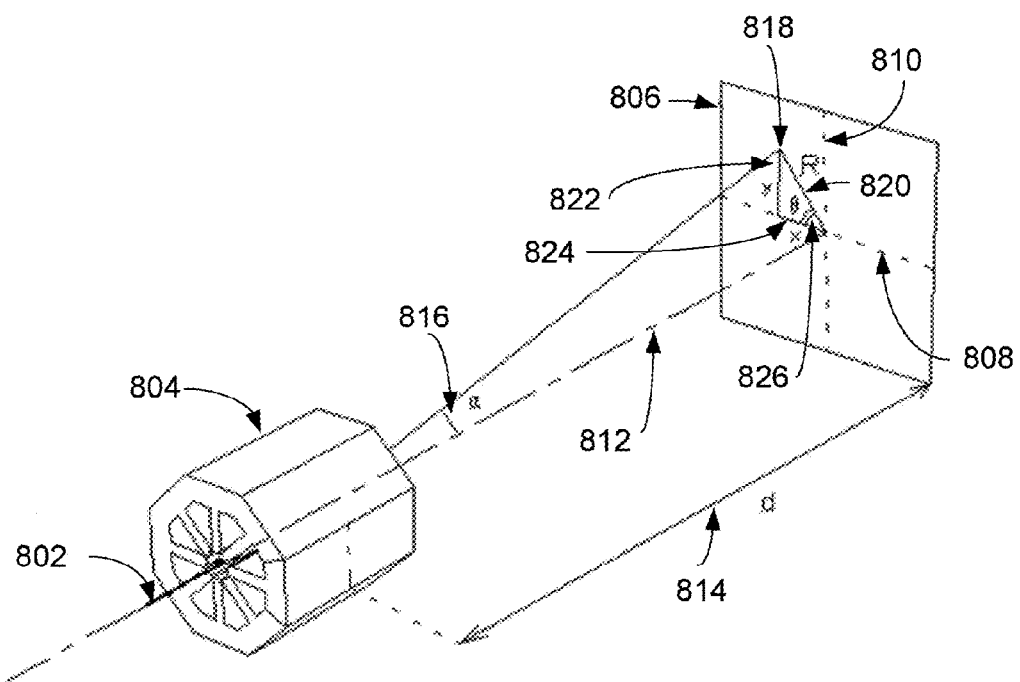
FIG. 8 presents an example illustration of an electromagnetic portion deflecting a beam of charged particles and the orientation of the charged particles with respect to a downstream plane, in accordance with an embodiment of the present invention.

FIG. 8 presents an example illustration of an electromagnetic portion deflecting a beam of charged particles and the orientation of the charged particles with respect to a downstream plane, in accordance with an embodiment of the present invention.

The illustration of FIG. 8 includes a charged particle beam 802, a multi-pole electromagnetic portion 804 and an intersect plane 806.

Charged particle beam 802, multi-pole electromagnetic portion 804 and intersect plane 806 may be orientated with respect to an x-axis 808, a y-axis 810 and a z-axis 812.

Multi-pole electromagnetic portion 804 may operate to receive and deflect charged particle beam 802.

Multi-pole electromagnetic portion 804 may be located a distance 814, denoted as d, from intersect plane 806 and with z-axis 812 traversing through its longitudinal center. Typical values for d may be in the range of 1 m to 10 m.

Charged particle beam 802 may be deflected from z-axis 812 in the plane of the deflection direction by an angle 816, denoted as α, and intersect plane 806 at a point 818. Typical values for a may be in the range of −10 degrees to +10 degrees.

Point 818 may be located a distance 822 from x-axis 808, a distance 824 from y-axis 810 and a distance 820, denoted as R, from z-axis 812. Furthermore, point 818 may be located at an angle 826, denoted as θ, with respect to x-axis 808.

Charged particle beam 802 may be considered as intersecting intersect plane 806 at a polar location as denoted by R and θ. The intersection of charged particle beam 802 with intersect plane 806 at point 818 may also be resolved into x and y coordinates.

Multi-pole electromagnetic portion 804 may operate to rotate a fixed strength dipole magnetic field to any angle and as a result deflect charged particle beam 802 to any angle. Furthermore, multi-pole electromagnetic portion 804 may control the deflection of charged particle beam 802 via parameters R and θ.

For multi-pole electromagnetic portion 804 operating sufficiently far from yoke saturation, the relationship between $I_p$ and the dipole magnetic field may be considered as linear with R a linear function of $I_p$. Thus, maintaining $I_p$ constant and incrementing θ transfers the location of point 818 (i.e. where charged particle beam 802 intersects intersect plane 806) in a circle about intersect plane 806. For any particular set of circumstances, point 818 may lie within a maximum diameter circle. The diameter may be set by d and α. In a non-limiting example, typical values for particle therapy are diameters of 100 cm and less, although some treatments such as the spine require larger fields. This may be achieved by increasing d because a may be constrained by practical magnet design issues. Furthermore, the maximum diameter of the circle may be dependant upon a particular configuration and associated circumstances. Non-limiting examples of circumstances contributing to the maximum diameter of the circle include particle beam magnetic rigidity, multi-pole electromagnetic portion 804 configuration, power supply and distance of electromagnetic portion from intersect plane 806. Charged particle beam 802 movement may not be dependant upon any particular axis.

Conversion from coordinates associated with intersect plane 806 defined by Cartesian coordinates x, y to polar parameters R, θ may be accomplished via conventional mathematical transformations. For small angles of deflection for α, the $I_p$, θ values for a given x,y position located on intersect plane 806 may be given by Equation (3) and Equation (4) shown below:

$$\theta = \sin^{-1}(y/\sqrt{(x^2+y^2)}) \quad (3)$$

$$I_p = C \cdot \alpha \quad (4)$$

Standard sign conventions may be applied to θ based upon whether point 818 lies within the right or left hand halves of intersect plane 806. The element C in Equation (4) may represent a proportionality constant. Non-limiting examples of parameters for determining the value of C include coil design, size of electromagnetic portion air gap, length of electromagnetic portion and permeability of the magnetic flux for the return yoke. Non-limiting examples of methods for determining the value of C include direct measurement or electromagnetic modeling and ray tracing. As a good approximation, α may be expressed in terms of the beam rotation angle θ (or angle 826) and other geometric parameters as given by Equation (5) below:

$$\alpha = \tan^{-1}(x/d)/\cos\theta \quad (5)$$

For Equation (5) d (or distance 814) may represent the displacement along z-axis 812 from the center of multi-pole electromagnetic portion 804 to intersect plane 806 and x (or distance 824) may represent the displacement along x-axis 808.

The power amplifiers connected to the coils for supplying power to electromagnetic portions may be of four-quadrant design for supporting a charged particle beam placement at any geometric location of intersect plane 806. The n/2 power amplifiers may provide high-current and be supplied via a single DC power supply with associated energy storage capacitors. The inductance of the electromagnetic portion may be considered an energy storage device which exchanges energy with the storage capacitors while maneuvering the charged particle beam. High efficiency may be experienced for a circular motion about z-axis 812, as the total energy stored in multi-pole electromagnetic portion 804 remains constant with small associated changes in electrical current, resulting in small power amplifier switching losses.

Dipole magnetic field quality improves with an increased number of poles. Furthermore, for most real-world cases, an eight pole electromagnetic portion may be considered adequate for practical and economic considerations. Furthermore, a six-pole electromagnetic portion may yield sufficient dipole magnetic field quality for many applications.

Figure 9:
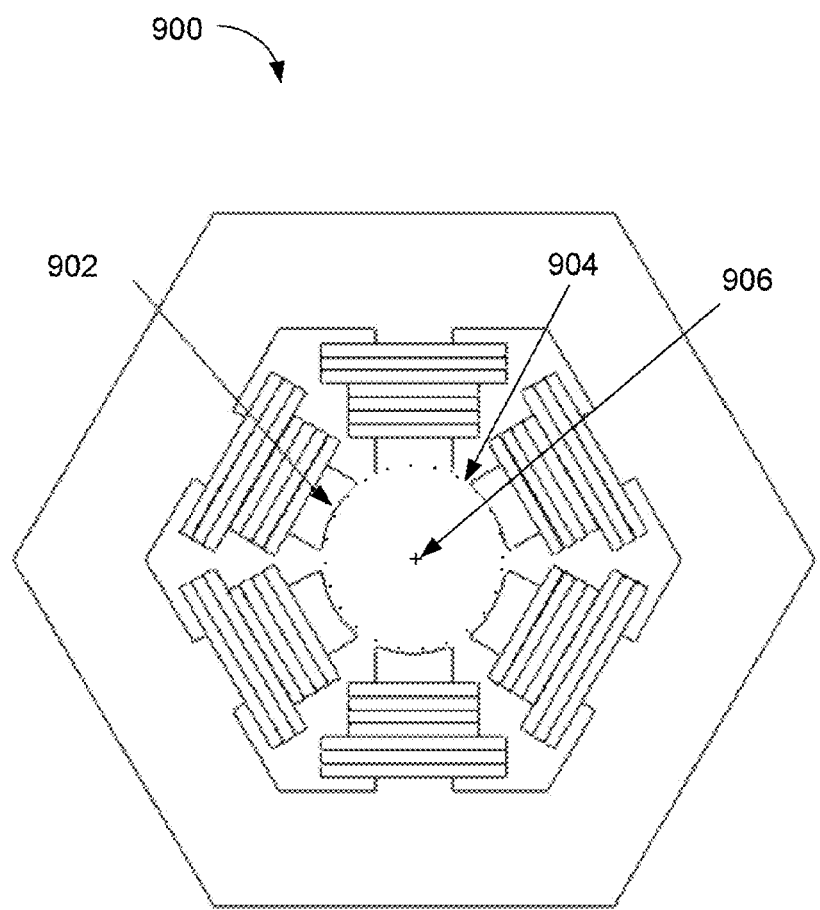
FIG. 9 presents a cross-section illustration of an example multi-pole deflection apparatus with modified pole tips for improving the quality of the associated dipole magnetic field for deflecting a charged particle, in accordance with an embodiment of the present invention.

FIG. 9 presents a cross-section illustration of an example multi-pole deflection apparatus with modified pole tips for improving the quality of the associated dipole magnetic field for deflecting a charged particle, in accordance with an embodiment of the present invention.

A multi-pole deflection apparatus 900 has a similar construction as sextupole deflection apparatus 400 (FIG. 4) except the pole tips, with a sampling denoted as a pole tip 902, may be configured with an associated circular profile in order to improve the quality of the dipole magnetic field. Pole tips shaped as shown for an inscribed circle 904 may operate to improve the magnetic field quality at distances removed from a central axis 906. Furthermore, the pole tips shaped for inscribed circle 904 may operate to reduce charged particle beam aberrations at larger angles of deflection.

Figure 10:
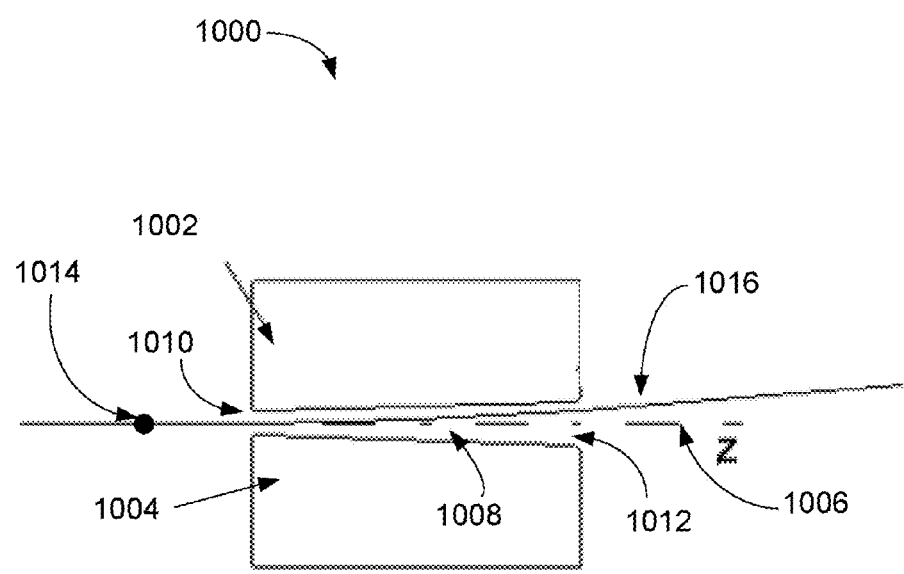
FIG. 10 presents an illustration of an example multi-pole deflection apparatus with modified air gaps between poles for providing greater clearance for a charged particle beam as it deflects into a magnetic dipole field, in accordance with an embodiment of the present invention.

FIG. 10 presents an illustration of an example multi-pole deflection apparatus with modified air gap between poles for providing greater clearance for a charged particle beam as it deflects in the magnetic dipole field, in accordance with an embodiment of the present invention.

A multi-pole deflection apparatus 1000 includes a multiplicity of poles (some not shown) with a sampling denoted as a pole 1002 and a pole 1004.

Pole 1002 and pole 1004 may be oriented with a z-axis 1006 running longitudinally through an air gap 1008 located between pole 1002 and pole 1004.

A charged particle 1014 may enter air gap 1008 at an entry gap 1010 and exit at an exit gap 1012. A smaller distance between pole 1002 and pole 1004 may be provided at entry gap 1010 than at exit gap 1012. Furthermore, the distance between pole 1002 and pole 1004 may increase as a charged particle progresses from entry gap 1010 to exit gap 1012. As a result of the magnetic field provided by multi-pole deflection apparatus 1000, charged particle 1014 may follow a trajectory path 1016.

Large deflection angles result in a charged particle beam coming in close proximity to poles. In order to reduce the risk of a charged particle beam coming in contact with a pole and an associated charged particle beam loss, the inscribed diameter for the air gap may be increased along the length of the electromagnetic portion. The associated flaring of the inscribed diameter may be continuous along the full length of the electromagnetic portion or may initiate at some distance along the length of the electromagnetic portion. The resulting deflection for a given set of excitation currents may be reduced by the associated flaring.

Figure 11:
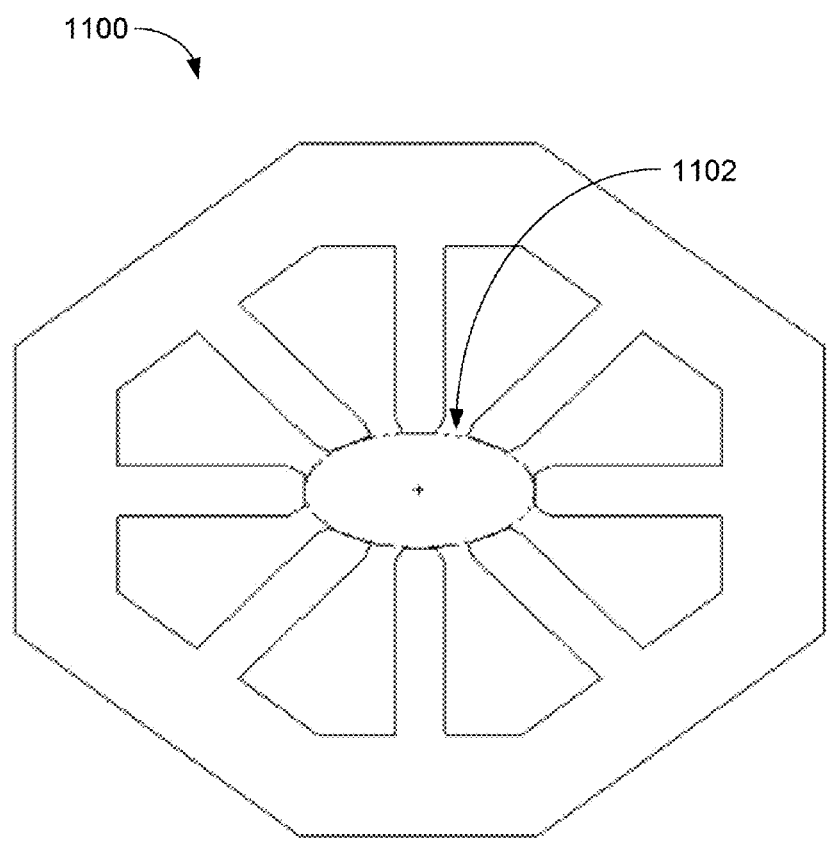
FIG. 11 presents a cross-section illustration of an example multi-pole deflection apparatus with a non-circular bore, in accordance with an embodiment of the present invention.

FIG. 11 presents a cross-section illustration of an example multi-pole deflection apparatus with a non-circular bore, in accordance with an embodiment of the present invention.

A multi-pole deflection apparatus 1100 has a similar construction as octupole deflection apparatus 500 (FIG. 5), except with a non-circular bore 1102. For this example, an elliptical bore has been presented for non-circular bore 1102, however any known geometrical shape may be applied.

An electromagnetic portion with a non-circular bore may operate in a similar manner as described previously for a circular bore (e.g. FIG. 5). For example, for an elliptical bore, a rotating magnetic field with constant $I_p$ generates an elliptical path at an intersection plane, rather than a circular path.

Coil currents may be delivered to the coils not conforming to the sinusoidal pattern described previously. Other patterns of coil currents introduce higher order terms into the magnetic field and result in distortion in the shape of the charged particle beam. In some embodiments additionally imposed pattern of currents may be non-sinusoidal or sinusoidal to produce beam shaping. In a non-limiting example an additional superimposed sinusoidal pattern, at twice the spatial frequency of the basic pattern that gives the dipole field, may produce a useful quadrupole field component that gives beam shaping typical of a quadrupole magnet. Application of particular patterns of coil currents may be applied in order to introduce deliberate charged particle beam shaping such as, but not limited to, the beam transverse shape to be more like a line than a circle. Furthermore, a separate power amplifier may be connected to individual coils, rather than to pairs of opposed coils as described previously, providing further control over charged particle beam shaping. In a non-limiting example, a useful use of this beam shaping capability is to make the quadrupole field component of this multipole magnet one half of a quadrupole doublet. The other member of the doublet would be a conventional quadrupole magnet structure positioned before the multipole magnet in the beam path. This combination may provide focusing in both transverse axes orthogonal to the beam axis, which is the typical function of a quadrupole doublet. The benefit is that the need for a second conventional quadrupole is avoided, and thus cost and space are saved.

For many applications, the ability to perform timely magnetic field changes may be required. A beam scanning magnetic apparatus may be considered as a non-limiting example for an application making use of a fast changing magnetic field. Furthermore, to support a fast changing magnetic field, the return yoke structure may be constructed from thin laminations in order to minimize losses and field distortions associated with eddy currents. Furthermore, as a non-limiting example, the yoke structure maybe constructed of laminated steel, ferrite or any material with relative permeability greater than 1. Furthermore, to support a fast changing magnetic field, the coils may have a relatively small number of turns in order to minimize the inductance. Furthermore, to support a fast changing magnetic field, the power amplifiers may support high current capability, typically hundreds of amperes, in order to support the small number of turns in the coils. Furthermore, to support a fast changing magnetic field, the power amplifiers may support a wide voltage range, typically up to +/−800V with currents up to 800 A, in order to allow the inductive load to transition to a new current level. Furthermore, to support a fast changing magnetic field, the power amplifiers may support a wide bandwidth, typically DC to a multiplicity of kilohertz in order to minimize the settling time after transitioning to a new current level.

Figure 12:
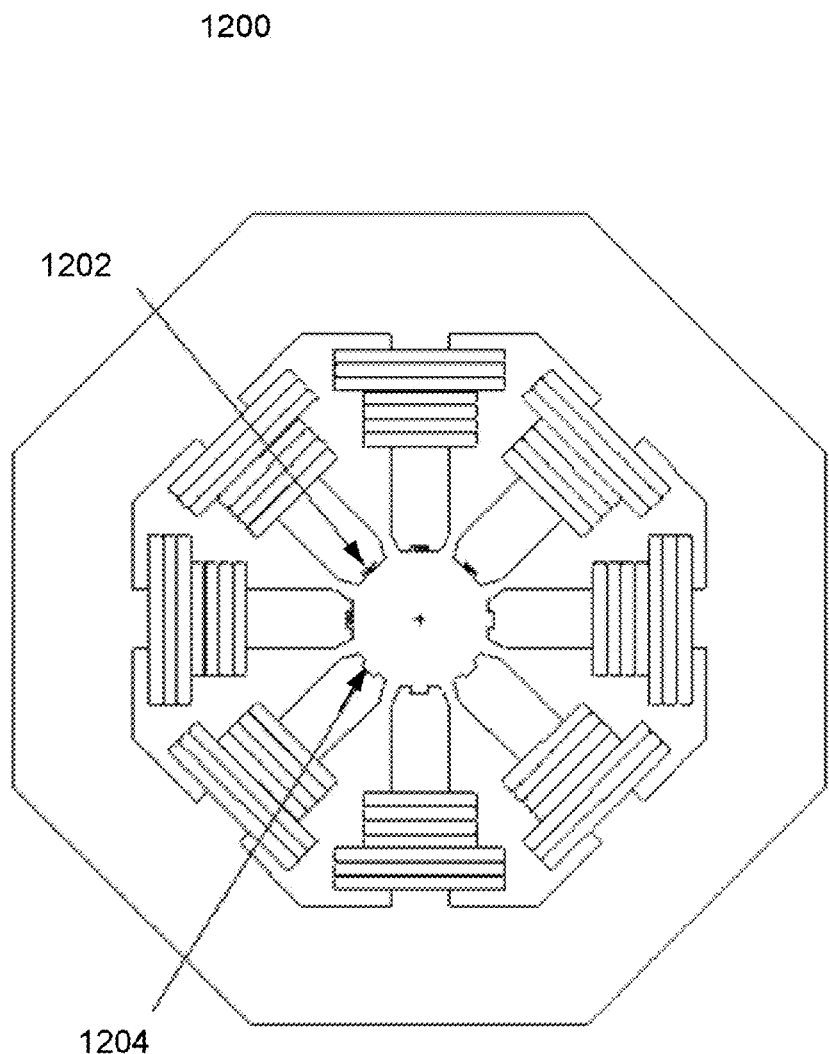
FIG. 12 presents a cross-section illustration of an example multi-pole deflection apparatus incorporating a Hall effect probe to provide magnet field feedback for monitoring and control, in accordance with an embodiment of the present invention.

FIG. 12 presents a cross-section illustration of an example multi-pole deflection apparatus incorporating a Hall effect probe to provide magnet field feedback for monitoring and control, in accordance with an embodiment of the present invention.

A multi-pole deflection apparatus 1200 has a similar construction as octupole deflection apparatus 500 (FIG. 5), except with a multiplicity of Hall effect probes, with a sampling denoted as a Hall effect probe 1202, configured in a multiplicity of recesses, with a sampling denoted as a recess 1204.

For applications where large magnetic field strengths may be required, assumptions previously described for a magnetic field as a linear function of $I_p$ may not hold. The magnetic field as a linear function of $I_p$ may also not hold for conditions of significant eddy currents and steel hysteresis. For these types of applications and conditions, Hall effect probe 1202 may be configured for accurately measuring magnetic fields. The signal provided by Hall effect probe 1202 may be used as a confirmatory function or as a process feedback for closed-loop electromagnetic field control. Hall effect probe 1202 may be positioned at the tips of individual poles in order to enable measurement of the individual contributions to the net magnetic field.

Those skilled in the art will readily recognize, in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Having fully described at least one embodiment of the present invention, other equivalent or alternative methods of performing electromagnetic deflection of a charged particle beam according to the present invention will be apparent to those skilled in the art. The invention has been described above by way of illustration, and the specific embodiments disclosed are not intended to limit the invention to the particular forms disclosed. For example, the particular implementation of the power amplifiers described with reference to FIG. 3 may vary depending upon the particular application the apparatus is to be applied. The exemplary power amplifiers described in the foregoing were directed to medical implementations; however, similar techniques may be demonstrated for other applications such as for semiconductor manufacture. Implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. An apparatus comprising:
   at least six electromagnetic portions disposed on a plane, each of said at least six electromagnetic portions being aligned with a radius emanating from an axis normal to said plane and being distanced from said axis to form a volume about said axis;
   at least six coils being configured for generating a dipole magnetic field in said volume in response to electrical current patterns applied to physically opposing coils, said dipole magnetic field comprising vectors being generally equal in magnitude with a same direction of orientation on said plane traversing said axis, said orientation being rotatable about said axis in response to a change in said current patterns to deflect a particle beam entering said volume in a direction away from said axis, each of said at least six coils being disposed about a one of said at least six electromagnetic portions; and
   a yoke structure being configured for returning a generated magnetic flux.

2. The apparatus as recited in claim 1, in which said at least six coils are further configured as at least three pairs of physically opposing coils, each of said at least three pairs being configured to be excited by a separate electrical current pattern.

3. The apparatus as recited in claim 2, in which said separate electrical current patterns comprise a sinusoidal component.

4. The apparatus as recited in claim 1, in which tips of said at least six electromagnetic portions that face said axis are shaped to affect the dipole magnetic field.

5. The apparatus as recited in claim 1, in which tips of said at least six electromagnetic portions that face said axis are shaped to vary the distance from said axis along a length of said tips to mitigate contact of said tips by said deflected particle beam.

6. The apparatus as recited in claim 1, in which said at least six electromagnetic portions are distanced from said axis to form a non-circular surface of said volume to correspond to a non-circular deflection pattern.

7. The apparatus as recited in claim 2, in which said separate electrical current patterns comprise a non-sinusoidal component to produce changes in a shape of the particle beam.

8. The apparatus as recited in claim 1, in which tips of said at least six electromagnetic portions that face said axis comprise devices for measuring said dipole magnetic field.

9. The apparatus as recited in claim 1, in which an amount of electromagnetic portions and an amount of coils is eight.

10. A system comprising:
at least six electromagnetic portions disposed on a plane, each of said at least six electromagnetic portions being aligned with a radius emanating from an axis normal to said plane and being distanced from said axis to form a volume about said axis;
at least six coils being configured for generating a dipole magnetic field in said volume in response to electrical current patterns applied to physically opposing coils, said dipole magnetic field comprising vectors being generally equal in magnitude with a same direction of orientation on said plane traversing said axis, said orientation being rotatable about said axis in response to a change in said current patterns to deflect a particle beam entering said volume in a direction away from said axis, each of said at least six coils being disposed about a one of said at least six electromagnetic portions;
a yoke structure being configured for returning a generated magnetic flux;
a plurality of power amplifiers for supplying said electrical current patterns;
a control system for monitoring and controlling operations of said power amplifiers; and
a power supply for powering at least said power amplifiers and said control system.

11. The system as recited in claim 10, in which said at least six coils are further configured as at least three pairs of physically opposing coils, each of said at least three pairs being configured to be excited by a separate one of said plurality of power amplifiers.

12. The system as recited in claim 11, in which said separate electrical current patterns comprise a sinusoidal component.

13. The system as recited in claim 10, in which tips of said at least six electromagnetic portions that face said axis are shaped to affect the dipole magnetic field.

14. The system as recited in claim 10, in which tips of said at least six electromagnetic portions that face said axis are shaped to vary the distance from said axis along a length of said tips to mitigate contact of said tips by said deflected particle beam.

15. The system as recited in claim 10, in which said at least six electromagnetic portions are distanced from said axis to form a non-circular surface of said volume to correspond to a non-circular deflection pattern.

16. The system as recited in claim 11, in which said separate electrical current patterns further comprise a non-sinusoidal component to produce changes in a shape of the particle beam.

17. The system as recited in claim 10, in which tips of said at least six electromagnetic portions that face said axis comprise devices for feedback to said control system.

18. The system as recited in claim 10, in which said at least six coils are further configured for generating said dipole magnetic field for use in particle therapy.

19. A method comprising steps of:
arranging at least six electromagnetic portions of a multi-pole electromagnet to be disposed on a plane where each of said at least six electromagnetic portions are aligned with a radius emanating from an axis normal to said plane and are distanced from said axis to form a volume about said axis;
configuring at least six coils for generating a dipole magnetic field in said volume in response to electrical current patterns comprising sinusoidal components being applied to physically opposing coils, said dipole magnetic field comprising vectors being generally equal in magnitude with a same direction of orientation on said plane traversing said axis, said orientation being rotatable about said axis in response to a change in said current patterns; and
exciting said at least six coils with said current patterns for rotating said dipole magnetic field to deflect a particle beam entering said volume to a desired position away from said axis.

20. The method as recited in claim 19, further comprising the step of applying a component to said electrical current patterns to shape the particle beam.

\* \* \* \* \*